United States Patent [19]

Duc

[11] Patent Number: 5,464,408
[45] Date of Patent: Nov. 7, 1995

[54] TRANSLUMINAL IMPLANTATION OR EXTRACTION DEVICE

[76] Inventor: Jerome Duc, Boliette 1, 1802, Corseaux, Switzerland

[21] Appl. No.: 891,514

[22] Filed: Jun. 1, 1992

(Under 37 CFR 1.47)

[30] Foreign Application Priority Data

Jun. 14, 1991 [SE] Sweden ................................. 9101839

[51] Int. Cl.⁶ ................................................. A61B 19/00
[52] U.S. Cl. ......................................... 606/108; 606/198
[58] Field of Search ........................ 128/3, 20, 749–754; 604/96, 104–109; 606/1, 106, 108, 110, 127, 190–198, 205–209; 623/1, 12, 900

[56] References Cited

U.S. PATENT DOCUMENTS

| | | |
|---|---|---|
| 3,397,699 | 8/1968 | Kohl . |
| 4,043,346 | 8/1977 | Mobley et al. . |
| 4,611,594 | 9/1986 | Grayback et al. ........... 606/127 |
| 4,990,151 | 2/1991 | Wallsten ..................... 606/108 |
| 4,997,435 | 3/1991 | Demeeter .................... 606/127 |
| 5,098,440 | 3/1992 | Hillstead ..................... 606/108 |
| 5,190,561 | 3/1993 | Graber ........................ 606/127 |
| 5,290,295 | 3/1994 | Querals et al. .............. 606/108 |

FOREIGN PATENT DOCUMENTS

| | | | |
|---|---|---|---|
| 364420 | 4/1990 | European Pat. Off. . | |
| 3909999 | 9/1990 | Germany . | |
| 1618398 | 1/1991 | U.S.S.R. | ................. 604/107 |

Primary Examiner—Stephen C. Pellegrino
Assistant Examiner—Glenn Dawson
Attorney, Agent, or Firm—Peter C. Richardson; Lawrence C. Akers; John L. LaPierre

[57] ABSTRACT

A device for transluminal extraction or implantation of a substantially tubular, radially expansible stent. The device includes a central tube surrounded by an exterior tube axially displaceable relative to the central tube and a plurality of axially extending gripping members coupled to the central tube at a distal end thereof. The gripping members are substantially evenly distributed around the periphery of the central tube and capable of outward expanding action of their distal ends when the central tube is displaced relative to the exterior tube. The gripping members are arranged in at least two concentric sets with a first set being radially displaced relative to a second set so as to substantially cover the gaps between adjacent gripping members of the first and second sets when in an expanded position. The sets of gripping members form a substantially closed distal end periphery when in the expanded position permitting a substantially continuous circumferential engagement around the stent.

10 Claims, 2 Drawing Sheets

1

TRANSLUMINAL IMPLANTATION OR EXTRACTION DEVICE

BACKGROUND OF THE INVENTION

The present invention relates to a device for transluminal extraction or implantation of a substantially tubular, radially expansible stent.

Devices for transluminal implantation of expanding stents or prostheses are previously known. Thus, U.S. Pat. No. 4,732,152 describes a device enabling transluminal implantation of self-expanding stents. The device described in said U.S. patent shows excellent performance in regard to enabling implantation of prostheses or stents in for example blood vessels or other ducts in living animal bodies. However, most implantation devices including that described in U.S. Pat. No. 4,732,152 suffer from the serious drawback of not enabling later extraction of an implanted prosthesis or stent. Such extraction of the implanted artifact will sometimes be necessary due to improper location or disturbances created by the presence of the stent.

In an attempt to solve the problem of extracting an implanted prosthesis or stent a device has been proposed, such as the one disclosed in published European patent application A1 0 364 420. Said device enabling transluminal implantation or extraction of radially self-expanding stents includes a central tube surrounded by an exterior tube axially displaceable relative to the central tube, and a plurality of axially extending spring members attached to the distal end of said central tube. These spring members are evenly distributed around the periphery of the central tube and capable of outwards springing action of their distal ends when retracting the exterior tube from the distal end of the central tube.

However, the device disclosed in said European patent application is associated with drawbacks in that the spring members engaging the stent from the outside in their expanded position are spaced apart so as not to cover the whole periphery of the stent causing deformation of the stent and also resulting in problems in the extraction procedure. This is particularly the case when operating with prostheses or stents of the type disclosed in U.S. Pat. No. 4,655,771. This particular type of prosthesis for use in transluminal implantation comprises a flexible tubular body composed of a braided arrangement of flexible thread elements involving free ends at the axial extremes of the prosthesis. In practical operation it has been found that using the device disclosed in European patent application A1 0 364 420 involves severe problems due to the fact that the spring members of said device in their expanded position cannot properly engage the end of the prosthesis in connection with the extraction procedure.

SUMMARY OF THE INVENTION

The present invention has for its main object to solve the problems associated with the prior art devices while enabling easy extraction of an implanted expanding stent whenever desired.

Another object of the invention is to provide for a device that can be used for implantation as well as extraction of a self-expanding stent.

Still another object of the invention is to provide a device which enables proper positioning of such self-expanding stent in connection with the implantation thereof.

For these and other objects which will be clear from the following description the invention provides a device for transluminal extractional implantation of a substantially tubular, radially expansible stent, comprising a central tube surrounded by an exterior tube which is axially displaceable relative said central tube, and a plurality of axially extending gripping members associated with or attached to said central tube at a distal end thereof. The gripping members are substantially evenly distributed around the periphery of the central tube and capable of outward expanding action of the their distal ends when retracting the exterior tube from the distal end of the central tube.

In the instant disclosure the expressions "distal" and "proximal" refer to the front end (position of gripping members) and the opposite rear end, respectively, of the associated construction detail or element.

The improvement introduced into the device of the present invention is constituted by the fact that the gripping members are arranged in at least two concentric sets, wherein every other set is circumferentially displaced relative the adjacent one so as to substantially cover the gaps between two adjacent members of the adjacent set when in an expanded position. In this manner the sets of gripping members form a substantially closed distal end periphery when in said expanded position which permits a substantially omnidirection of engagement around the stent.

Although as indicated above the number of gripping member sets has no absolute upper limit it is preferred to use as few sets as required to cover the gaps between adjacent gripping members when in an expanded position, and for most practical applications two concentric sets of gripping members are sufficient for obtaining the advantage of the invention.

In one embodiment of the device according to the present invention an inner set of gripping members is made integral with the central tube, and in such embodiment said members may be formed by cutting up axially extending slits at the distal end of the central tube followed by outwardly biased deformation of the gripping members to enable the expanding action when removing restraint from said members.

In such embodiment an outer set of gripping members may be constituted by a sleeve surrounding the distal end of the central tube. Also in this embodiment the gripping members may be formed by cutting up axially extending slits at the distal end of the sleeve.

In another embodiment of the device according to the present invention both sets of gripping members may be formed by cutting up axially extending slits at the distal ends of two concentric sleeves associated with the central tube.

In order to facilitate penetration between an implanted stent and the surrounding lumen wall it is preferred to provide the gripping members with distal ends that are pointed or rounded.

Furthermore, in order to improve the engagement of the gripping members with the stent in connection with for example extraction of the stent it is preferred that at least two of diametrically positioned gripping members are provided with inwardly extending bent sections or hooks.

In the device according to the invention there may be provided viewing means, such as an endoscope or a telescope, positioned inside the central tube and axially displaceable therein.

So as to enable introduction of the device of the invention into tortuous bodily ducts it is preferred to make the concentric members of flexible materials. When using an endoscope or telescope also such means are to be made of flexible materials.

With regard to the number of gripping members in each set it is preferred to use at least 3 members in each set. The upper limit is not critical but a practical upper limit may be from about 10 to about 15 members in each set.

The invention also covers an apparatus for implanting a substantially tubular, radially expansible stent, said apparatus comprising a device as described above in combination with such a stent positioned between the gripping members in a contracted state and the exterior tube. In such apparatus the stent is preferably of the self-expanding type, and its is especially preferred to use stents of the type described in U.S. Pat. No. 4,655,771, the full contents of which are incorporated herein by reference.

BRIEF DESCRIPTION OF THE DRAWINGS

The present invention will now be described by a non-limiting example with reference to the appended drawing, wherein.

DETAILED DESCRIPTION OF A PREFERRED EMBODIMENT

Figure 1:
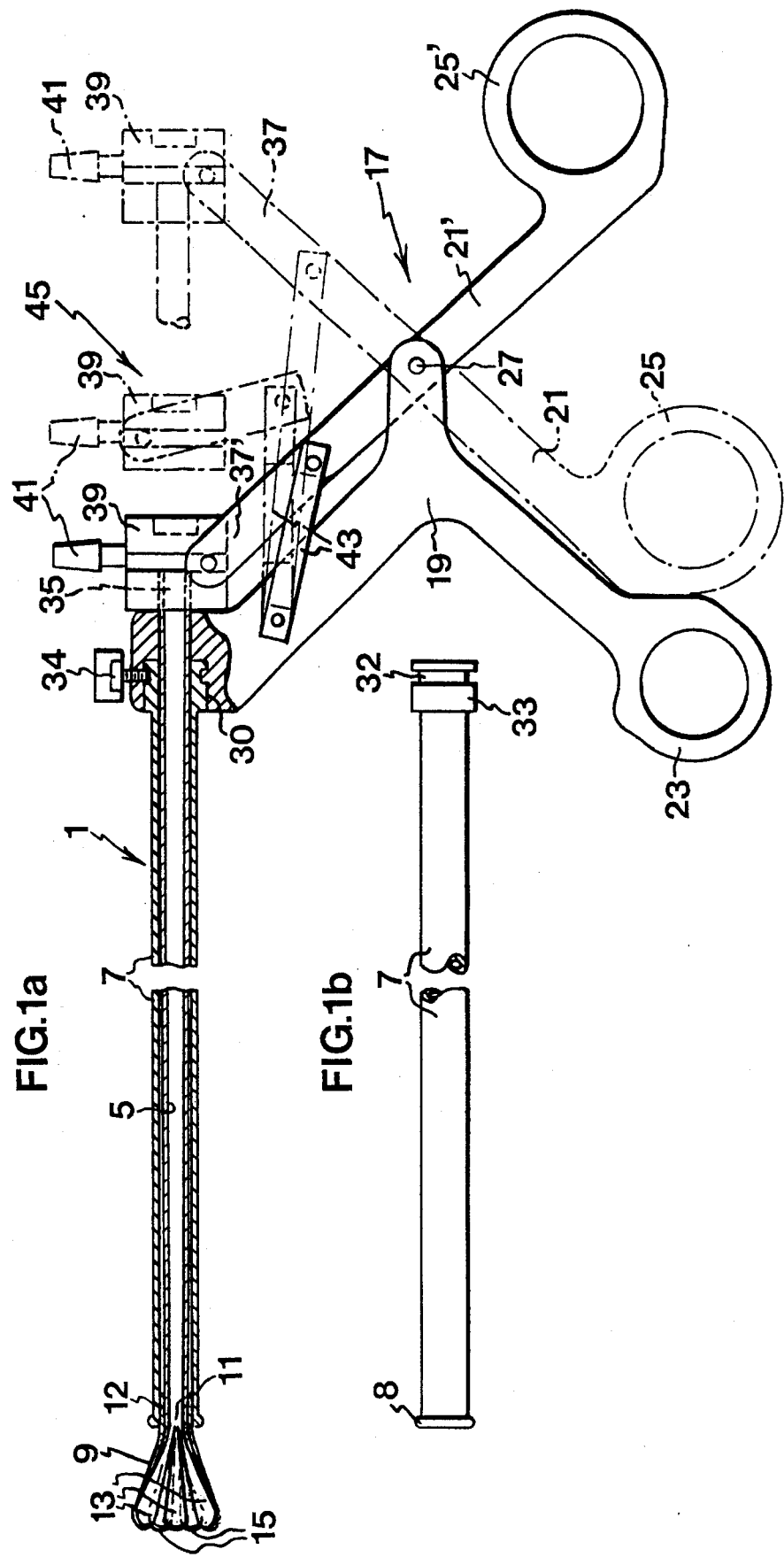
FIG. 1a is a diagrammatic side-view, partly in section, of a preferred embodiment of the device of the invention.
FIG. 1b shows a detail of the device of FIG. 1a, namely the exterior tube detached from the device.

The device shown in FIG. 1a is generally designated 1 and the device comprises two flexible tubes, one central tube 5 and a surrounding exterior tube 7. Said tubes are substantially coextensive except for the fact that the exterior tube 7 is shorter than central tube 5 by a distance enabling association with the proper manoeuvering means 45 at the rear ends thereof. The exterior tube 7 is shown detached from the instrument proper in FIG. 1b. At the distal end exterior tube 7 is provided with an enlargement 8, whereas its proximal end carries an enlarged end piece 33 provided with a circumferentially extending groove 32 for a purpose to be explained further below.

Figure 2:
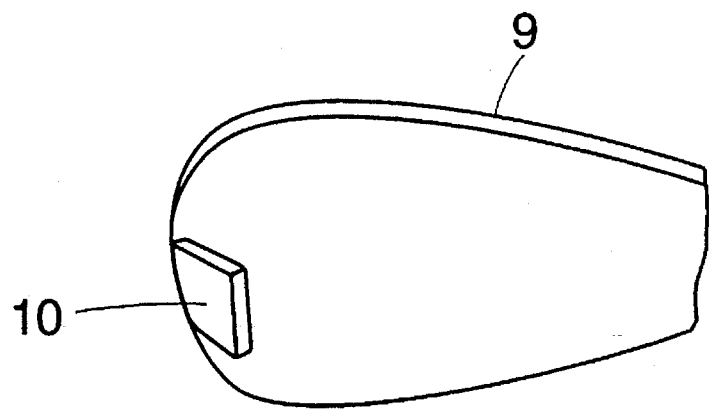
FIG. 2 is an enlarged, partial, schematic view showing a gripping member of the device having an inwardly extending hook.
Figure 3:
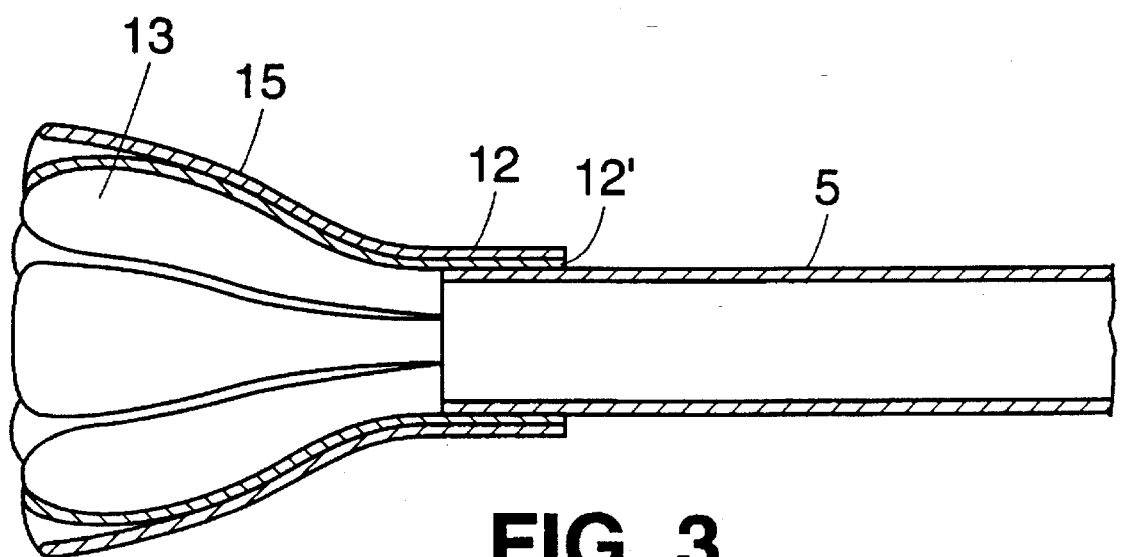
FIG. 3 is an enlarged, partial, schematic view illustrating another configuration of sets of gripping members.

Reverting to FIG. 1a, central tube 5 is provided with two sets 13, 15 of gripping members 9 at its distal end 11. The innermost set 13 of gripping members 9 are integral with central tube 5 in that they have been formed by cutting up axially extending slits at the distal end 11 of tube 5. The members or fingers thus formed are then subjected to outwardly biased deformation to take the position as shown in FIG. 1a when in a released state. As shown in FIG. 2, gripping member 9 could include an inwardly extending bent section or hook 10, the function of which will be indicated further below.

In the embodiment shown in FIG. 1a gripping members 9 are assembled in two concentric sets 13, 15. The outer set 15 of gripping members 9 are integral with a sleeve 12 attached to the outside of central tube 5 at the distal end 11 thereof. In the same way as the inner set 13 of gripping members 9 have been formed by cutting up slits in central tube 5, the outer set 15 of gripping members 9 have been formed by cutting up axially extending slits at the distal end of sleeve 12. In an alternative embodiment both sets of gripping members may be formed by using two concentric sleeves wherein axially extending slits at the distal ends thereof have been provided to form the gripping members. In relation to each other the two sets 13, 15 of gripping members 9 are circumferentially off set so that gripping members 9 of the inner set 13 substantially cover the gaps between the gripping members 9 of the outer set 15 when in an expanded state. In this manner the distal ends of gripping members 9 together form a circumferentially substantially continuous ring resulting in the advantages gained by the present invention. At the rear end of tubes 5, 7 the device comprises scissor-like operating means generally designated 17 said means comprising two legs 19, 21, each having a loop-handle 23, 25 and said legs 19, 21 are pivotally joined by a swivel pin 27. The proximal end of exterior tube 7 with its enlarged end piece 33 is attached to the upper part of left hand leg 19. Said proximal end of tube 7 is inserted into a recess 30 at the upper end of leg 19 and is maintained in a fixed position in said recess by a locking screw 34 engaging with groove 32.

The proximal end 35 of central tube 5 extends backwardly through the upper end of leg 19 and is pivotally attached to the upper end 37 of the other leg 21 via another end piece 39. Said end piece 39 contains inlet means 41 for the supply of fluid, such as a contrast medium or a flush liquid, that can be passed up to the distal end of the instrument through central tube 5.

Operating means 17 are shown in FIG. 1a in two extreme positions, one position (21', 25', 37') wherein gripping members 9 extend outside of the distal end of exterior tube 7, and a second position (21, 25, 37), where central tube 5 by operation of leg 21 has been moved rearwardly whereby gripping members 9 are contained within exterior tube 7 in a collapsed position. FIG. 1a, furthermore, shows an intermediate position indicated 45, where gripping members 9 rest within the distal end of tube 7 in a fixed position. This fixed intermediate position 45 is obtained by a safety catch 43 keeping the two legs 19, 21 in a position fixed relative to each other. This intermediate position is used in the critical stage of operation when a stent is to be implanted at the proper place within a bodily duct and it is essential that no wrong movements are involuntarily made.

The function of the device described and shown in the drawings is briefly as follows.

The use of a stent of the type described in U.S. Pat. No. 4,655,771 is assumed in relation to the function of device 1 according to the invention. With the gripping members 9 located in the position shown in FIG. 1a the rear end of a stent is accommodated within gripping members 9, and then using the operating means 17 central tube 5 is moved rearwardly to arrive at a position where gripping members 9 together with the stent are accommodated within exterior tube 7. The concentric tubes 5, 7 are now ready for entering a bodily duct wherein the stent is to be implanted.

When approaching the correct site of implantation the scissors-like means 17 are brought to the intermediate position 45 and this position is then fixed by means by safety catch 43. When the correct position has been reached the safety pin 43 will be released and central tube 5 moved forward to release the stent and the gripping members 9. The instrument can now be removed from the bodily duct leaving the stent behind at the desired location.

When a stent of the type referred to is to be extracted from the site of implantation the operation is repeated, this time by introducing the device into the bodily duct in question without a stent applied at the distal end thereof. When reaching the site of implantation gripping members 9 are again released to the position shown in FIG. 1a. Gripping members 9 are capable of exerting an outward force sufficient to widen the lumen wall so that they can move on to the rear end of the stent between the lumen wall and the stent proper. Thus, the instrument is moved so that the tips of gripping members 9 engage the proximal end of the implanted stent by engagement from the outside of said end of the stent in a position between the stent and the surrounding lumen wall. Two or more gripping members 9 could include hooks 10 as shown in FIG. 2 in order to improve the engagement of the gripping members with the stent. By again retracting central tube 5 gripping members 9 cause contraction of the proximal end of the stent while moving inside exterior tube 7 and the instrument together with the contracted stent can be withdrawn from the bodily duct without damaging the surrounding lumen wall.

By using the arrangement of at least two concentric sets of gripping members substantially covering the whole periphery when in an expanded state the problems arising in engaging the end of the stent will be greatly reduced and even eliminated. To facilitate proper location of the stent in connection with implantation thereof and to facilitate locating the distal end of device 1 in operating same it is preferred to provide the central tube 5 with radial openings at the distal end thereof. Alternatively, said central tube 5, at least at the distal end thereof, can be made of a transparent material enabling proper position of the device under operation. If necessary both tubes 5, 7 can be made of a transparent material or be provided with radially directed, juxtaposed openings at the distal ends thereof. An endoscope or other viewing apparatus could be inserted into the proximal end of the device and advanced axially through central tube 5 to a location for direct observation to ensure proper stent positioning or stent engagement.

It is to be noted that the present invention is in no way limited to the embodiments described above. Thus, any suitable materials can be used for different parts of the device and thus rigid materials are useful in many cases but flexible materials are useful as well to reach locations of different types of lumen that are difficult to get access to. Furthermore, the invention is useful not only with regard to the type of stents described in U.S. Pat. No. 4,655,771, although the device of the invention is particularly useful in relation to handling of such a stent.

I claim:

1. A device for transluminal extraction or implantation of a substantially tubular, radially expansible stent, comprising a central tube having a periphery and being surrounded by an exterior tube axially displaceable relative to said central tube, and a plurality of axially extending gripping members attached to said central tube at a distal end thereof, each of said gripping members having a distal end, said gripping members being substantially evenly distributed around the periphery of said central tube and adapted for outward expansion of their distal ends when said central tube is displaced relative to said exterior tube said gripping members being arranged in at least two concentric sets, with a first set being radially displaced relative to a second set to substantially cover one or more gaps between adjacent gripping members of said first and second sets when in an expanded position, said sets of gripping members thereby forming a substantially closed distal end periphery when in said expanded position permitting a substantially continuous circumferential engagement about at least a portion of said stent.

2. The device according to claim 1 wherein said gripping members are arranged in two concentric sets.

3. The device according to claim 1 wherein an inner set of gripping members is integral with said central tube, and is formed by cutting axially extending slits at the distal end of said central tube followed by outward permanent deformation to enable said outward expansion.

4. The device according to claim 1 wherein an outer set of gripping members comprises a sleeve disposed about the distal end of said central tube, the gripping members of said outer set being formed by cutting axially extending slits at a distal end of said sleeve.

5. The device according to claim 1 wherein the distal ends of said gripping members are configured to facilitate location of said gripping members between said stent and a surrounding lumen wall.

6. The device according to claim 1 wherein at least two diametrically positioned gripping members are provided with inwardly extending hooks for improving the engagement with said stent.

7. The device according to claim 1 where said device is adapted to accommodate viewing means positionable inside the central tube and axially displaceable therein.

8. The device according to claim 1 wherein the concentric sets of said gripping members are made of flexible materials enabling bending of the device under operation.

9. The device according to claim 1 wherein said gripping members in each set number at least 3.

10. The device according to claim 1 wherein an inner set and an outer set of gripping members comprise two concentric sleeves disposed about the distal end of said central tube, the gripping members of said inner and said outer set being formed by cutting axially extending slits at distal ends of said sleeves.

* * * * *